United States Patent [19]

Greenwald

[11] 4,056,539

[45] Nov. 1, 1977

[54] NAPHTHALIDE INDICATOR DYES

[75] Inventor: Richard B. Greenwald, Lexington, Mass.

[73] Assignee: Polaroid Corporation, Cambridge, Mass.

[21] Appl. No.: 669,190

[22] Filed: Mar. 22, 1976

Related U.S. Application Data

[63] Continuation-in-part of Ser. No. 520,248, Nov. 4, 1974, abandoned, which is a continuation-in-part of Ser. No. 204,350, Dec. 2, 1971, Pat. No. 3,862,128.

[51] Int. Cl.² ............................................ C07D 209/18
[52] U.S. Cl. ................................ 260/326.14 R; 96/3; 96/29 R; 96/29 D; 260/326.12 R
[58] Field of Search .............. 260/326.12 R, 326.14 R

[56] References Cited

U.S. PATENT DOCUMENTS

| | | | |
|---|---|---|---|
| 3,816,124 | 6/1974 | Karger et al. | 260/326.14 R |
| 3,816,453 | 6/1974 | Karger et al. | 260/326.14 R |
| 3,941,807 | 3/1976 | Borror | 260/326.14 R |

Primary Examiner—Dolph H. Torrence
Attorney, Agent, or Firm—Sybil A. Campbell

[57] ABSTRACT

This invention relates to indole (na) phthalide indicator dyes substituted with a particular class of hydrogen bonding groups, such as, perhaloalkyl carbinols. These dyes are useful as optical filter agents in photographic processes to protect a selectivity exposed photosensitive material from further exposure during processing in the presence of incident light.

6 Claims, No Drawings

NAPHTHALIDE INDICATOR DYES

CROSS-REFERENCE TO RELATED APPLICATIONS

This application is a continuation-in-part of copending application Ser. No. 520,248 filed Nov. 4, 1974, now abandoned, which in turn is a continuation-in-part of application Ser. No. 204,350 filed Dec. 2, 1971, now U.S. Pat. No. 3,862,128 issued Jan. 21, 1975.

BACKGROUND OF THE INVENTION

1. Field of the Invention

The present invention relates to novel chemical compounds, and more specifically, it relates to a new class of indicator dyes. In a particular aspect is relates to indicator dyes possessing certain hydrogen-bonding substituents useful as optical filter agents in photographic processes for protecting an exposed photosensitive material from post-exposure fogging during development in the presence of extraneous incident light.

2. Description of the Prior Art

A number of photographic processes by which images may be developed and viewed within seconds or minutes after exposure have been proposed. Such processes generally employ a processing composition which is suitably distributed between two sheet-like elements, the desired image being carried by one of said sheet-like elements. The resulting images may be in black-and-white, e.g., in silver, or in one or more colors. Processing may be conducted in or outside of a camera. The most useful of such processes are the diffusion transfer processes which have been proposed for forming silver or dye images, and several of these processes have been commericalized. Such processes have in common the feature that the final image is a function of the formation of an image-wise distribution of an image-providing reagent and the diffusion transfer of said distribution to or from the stratum carrying the final image, whether positive or negative.

U.S. Pat. No. 3,415,644 discloses a composite photosensitive structure, particularly adapted for use in reflection type photographic diffusion transfer color processes. This structure comprises a plurality of essential layers including, in sequence, a dimensionally stable opaque layer; one or more silver halide emulsion layers having associated therewith dye image-providing material which is soluble and diffusible, in alkali, at a first pH, as a function of the point-to-point degree of its associated silver halide emulsion's exposure to incident actinic radiation; a polymeric layer adapted to receive solubilized dye image-providing material diffusing thereto; a polymeric layer containing sufficient acidifying capacity to effect reduction of a processing composition from the first pH to a second pH at which the dye image-providing material is substantially nondiffusible; and a dimensionally stable transparent layer. This structure may be exposed to incident actinic radiation and processed by interposing, intermediate the silver halide emulsion layer and the reception layer, an alkaline processing composition providing the first pH and containing a light-reflecting agent, for example, titanium dioxide to provide a white background. The light reflecting agent (referred to in said patent as an "opacifying agent") also performs an opacifying function, i.e., it is effective to mask the developed silver halide emulsions and also acts to protect the photoexposed emulsions from postexposure fogging by light passing through the transparent layer if the photo-exposed film unit is removed from the camera before image formation is complete.

In a preferred embodiment, the composite photosensitive structure includes a rupturable container, retaining the alkaline processing composition having the first pH and light-reflecting agent, fixedly positioned extending transverse a leading edge of the composite structure in order to effect, upon application of compressive pressure to the container, discharge of the processing composition intermediate the exposed surfaces of the reception layer and the next adjacent silver halide emulsion.

The liquid processing composition distributed intermediate the reception layer and the silver halide emulsion, permeates the silver halide emulsion layers of the composite photosensitive structure to initiate development of the latent images contained therein resultant from photoexposure. As a consequence of the development of the latent images, dye image-providing material associated with each of the respective silver halide emulsion layers is individually immobilized as a function of the point-to-point degree of the respective silver halide emulsion layer photo-exposure, resulting in imagewise distributions of mobile dye image-providing materials adapted to transfer, by diffusion, to the reception layer to provide the desired transfer dye image. Subsequent to substantial dye image formation in the reception layer, a sufficient portion of the ions of the alkaline processing composition transfers, by diffusion, to the polymeric neutralizing layer to effect reduction in the alkalinity of the composite film unit to the second pH at which dye image-providing material is substantially non-diffusible, and further dye image-providing material transfer is thereby substantially obviated.

The transfer dye image is viewed, as a reflection image, through the dimensionally stable transparent layer against the background provided by the reflecting agent, distributed as a component of the processing composition, intermediate the reception layer and next adjacent silver halide emulsion layer. The thus-formed stratum effectively masks the residual dye image-providing material retained in association with the developed silver halide emulsion layer subsequent to processing.

In U.S. Pat. No. 3,647,347 issued Mar. 7, 1972 to Edwin H. Land, an organic light-absorbing reagent (or optical filter agent), such as dye, which is present as a light-absorbing species at the first pH and which may be converted to a substantially non-light-absorbing species at the second pH is used in conjunction with the light-reflecting agent to protect the selectively exposed silver halide emulsions from post-exposure fogging when development of the photoexposed emulsions is conducted in the presence of extraneous incident actinic radiation impinging on the transparent layer of the film unit.

In U.S. Pat. No. 3,702,244 issued Nov. 7, 1972, pH-sensitive dyes which contain at least one indole radical bonded by the 2- or 3-position to a ring-closing moiety are disclosed as useful as optical filter agents for absorbing incident radiation actinic to selectively exposed photosensitive materials within a predetermined wavelength range in the shorter wavelength region of the visible spectrum.

In U.S. Pat. No. 3,702,245 issued Nov. 7, 1972, pH-sensitive dyes derived from certain hydroxy-substituted carbocyclic aryl compounds, viz., particular phenols and naphthols are disclosed as useful as optical filter agents for absorbing incident radiation actinic to selectively exposed photosensitive materials within a predetermined wavelength range in the longer wavelength region of the visible spectrum.

The present invention is concerned with certain of the dyes disclosed in the aforementioned patents, namely, indicators substituted with a certain class of hydrogen bonding groups.

SUMMARY OF THE INVENTION

It is the primary object of the present invention to provide a novel class of indicator dyes.

It is another object of the present invention to provide a novel class of indicator dyes useful as optical filter agents in photographic processes for preventing post-exposure fogging of a selectively exposed photosensitive material during development in the presence of incident light.

It is a further object of the present invention to provide products, compositions and processes for the development of photosensitive materials in which the novel indicator dyes are used.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, there is provided a novel class of indicator dyes substituted with certain carbinol and other groups as hydrogen bonding substituents. These indicator dyes will be defined with greater particularity hereinafter.

Like pH sensitive dyes, generally, the dyes of the present invention exhibit reversibly alterable spectral absorption characteristics in response to changes in environmental pH. They have a colored, light-absorbing form in alkaline media at a first pH value above their pKa and a substantially colorless form, i.e., a form which is substantially non-light-absorbing in the visible spectrum at a second pH below their pKa. By pKa is meant the pH at which about 50% of the dye is present in its light-absorbing form and about 50% is present in its non-light-absorbing form.

It will be appreciated that such compounds will find utility in titrations and other analytical procedures where pH sensitive indicator dyes are commonly employed, for example, to measure changes in pH value as reflected by the change in color of the dye from one color to another or from colored to colorless or vice versa. The indicator dyes of the present invention, however, are especially useful as optical filter agents in photographic processes where development of a selectively exposed photosensitive material is performed at least in part outside the confines of a camera in the presence of extraneous incident actinic radiation.

For a fuller understanding of the nature and objects of the invention, reference should be had to the following detailed description.

DESCRIPTION OF THE PREFERRED EMBODIMENTS

Indicator dyes as exemplified by phthaleins, for example, phenolphthalein and 1-naphtholphthalein, are well known. Typically, these dyes possess two color-producing radicals, such as two p-hydroxyphenyl radicals bonded to a ring-closing moiety, such as, a phthalide.

The present invention is concerned with indicator dyes substituted with a certain class of hydrogen bonding groups comprising an alkyl radical substituted with an —OH, —SH, —NH$_2$ or =O group together with an electron-withdrawing group, preferably, a per-halomethyl group wherein halo is F, Cl, Br or combinations thereof. These groups are used for forming an intramolecular hydrogen bond with an appropriately positioned atom, and in a particular aspect, are used for forming an intramolecular hydrogen bond with the functional proton of a color-producing radical of an indicator dye, e.g., the functional —OH of a p-hydroxyphenyl radical to raise the pKa of the dye. Preferably, the pH sensitive dyes of the present invention are 3,3-disubstituted phthalides and 3,3-disubstituted naphthalides wherein the 3,3 substituents, the same or different, are cyclic radicals at least one of which is a color-producing radical.

Typical of such indicator dyes are those represented by the following formula:

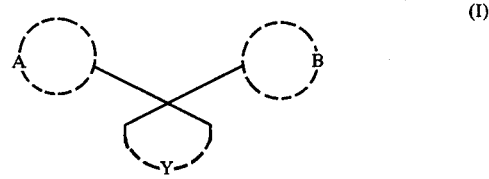
(I)

wherein A and B represent color producing radicals, the same or different, and Y represents a ring-closing moiety, preferably a phthalide or a naphthalide, one of said A and B radicals possessing a hydrogen bonding group.

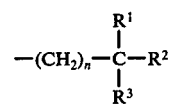

wherein R$^1$ is —OH, —SH or —NH$_2$; R$^2$ is hydrogen, alkyl, aryl, alkaryl or an electron-withdrawing group; R$^1$ and R$^2$ when taken together represent =O; R$^3$ is an electron-withdrawing group; and $n$ is an integer 0 or 1.

Illustrative A and/or B radicals include heterocyclic aryl radicals containing O, S, N, P or combinations thereof in the heterocyclic ring, for example, N-heterocyclic aryl radicals derived from indole, such as, indolyl; pyrrole, such as, pyrryl; carbazole, such as, carbazolyl; and carbocyclic aryl radicals derived from compounds of the benzene and naphthalene series, substituted and unsubstituted, for example, p-substituted carbocyclic aryl radicals, such as, p-hydroxy and p-amino phenyl and naphthyl radicals. The preferred ring-closing moieties may be represented by the formula,

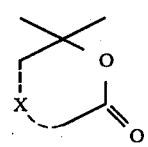

wherein X represents the carbon atoms necessary to complete phthalide or naphthalide.

The substituent R³ of the hydrogen bonding group may be any electron withdrawing group, i.e., any group with a positive sigma value as defined by Hammett's Equation. Such groups are well known in the art and include, for example, carboxy;, cyano; nitro; carbethoxy; sulfonyl; acyl and its derivatives, and as noted above, preferably is perhalomethyl, such as trifluoromethyl, difluorochloromethyl and difluorobromomethyl.

The substituent R² of the hydrogen bonding group may be any electron-withdrawing group, such as those enumerated above or any alkyl, aryl or alkaryl group including branched or straight chain alkyl, and preferably alkyl containing 1 to 20 carbon atoms, e.g., methyl, ethyl, isopropyl, n-butyl, t-butyl, hexyl, octyl, dodecyl, hexadecyl, octadecyl and eicosanyl; aryl, preferably phenyl and naphthyl; and alkaryl, preferably alkyl-substituted phenyl containing up to 20 carbon atoms, eg., p-octylphenyl, p-dodecylphenyl, p-methylphenyl, p-ethylphenyl; p-hexylphenyl and p-tetradecylphenyl.

Illustrative hydrogen bonding groups of the above-denoted class include:

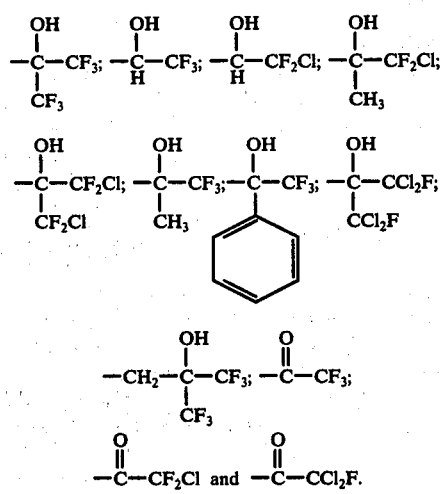

Among the classes of indicator dyes encompassed by formula I which are particularly useful as optical filter agents in photographic processes are phthalides and naphthalides wherein:

a. the A and B radicals both are 4'-hydroxy-1'-phenyl radicals or preferably are 4'-hydroxy-1'-naphthyl radicals, at least one of the A and B radicals possessing a hydrogen bonding group of the above-denoted class in the 3'-position;

b. one of the A and B radicals is a 4'-hydroxy-1'-phenyl or a 4'-hydroxy-1'-naphthyl radical and the other is an indol-3-yl radical, one or both of the A and B radicals possessing a hydrogen bonding group of the above-denoted class which is substituted in the 3'-position of the phenyl (or naphthyl) radical and in the 2- or 7-position of the indol-3-yl radical; and c. the A and B radicals both are indol-3-yl radicals, at least one of the A and B radicals possessing a hydrogen bonding group of the above-denoted class in the 2- or 7-position, preferably the 7-position.

In a particularly preferred embodiment, the indicator dyes of the subject invention are the naphthalides as represented in the following formula:

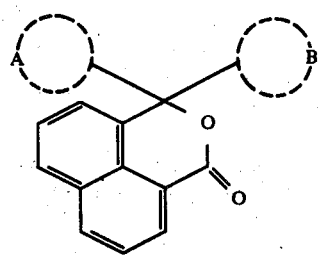

(II)

a'. wherein A and B are

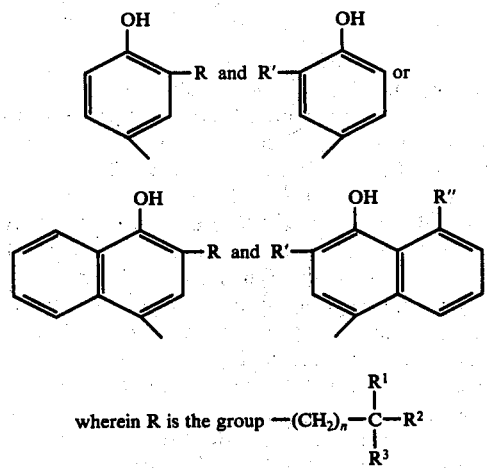

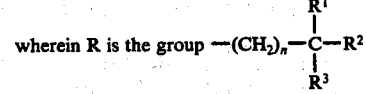

wherein R is the group wherein R¹ is —OH, R² is hydrogen, alkyl having 1 to 20 carbon atoms, aryl selected from phenyl and naphthyl, alkyl-substituted phenyl having up to 20 carbon atoms or perhalomethyl, R¹ and R² when taken together represent =O, R³ is perhalomethyl, and n is an integer 0 or 1 and R' and R" each are selected from hydrogen, carboxy, hydroxy, o-hydroxyphenyl, sulfonamido, sulfamoyl and said group

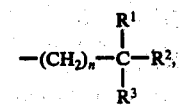

at least one of said R' and R" being hydrogen;
b'. wherein A is selected from

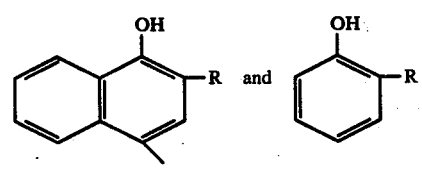

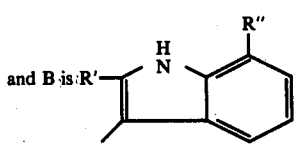

wherein R, R' and R" have the same meaning given above, at least one of R' and R" being hydrogen; and
c'. wherein A and B are

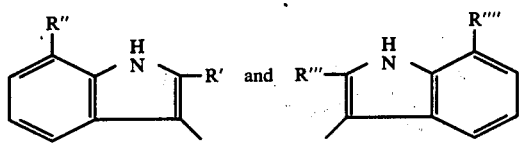

wherein R' and R" have the same meaning given above, at least one of R' and R" being hydrogen and one of R''' and R'''' is said group

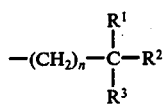

and the other is hydrogen.

The indicator dyes defined above and as represented in the foregoing formulae may contain substituents other than those specified on the A and/or B radicals and/or on the ringclosing moiety as may be desired which do not interfere with the function of the dye for its selected ultimate use. Where it is desired that the indicator dye be substantially immobile or non-diffusible in the processing solution, it may be substituted with a bulky group, such as, a long chain substituent, e.g., dodecyloxy, hexadecyl or dodecylphenyl. Also, it may be substituted with solubilizing groups, e.g., carboxy or sulfonic acid groups to adjust the solubility in a given solution.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as, phenyl and naphthyl; aralkyl and alkaryl, such as, benzyl, phenethyl, phenylhexyl, p-octylphenyl, p-dodecylphenyl; alkoxy, such as, methoxy, ethoxy, butoxy, 1-ethoxy-2-(β-ethoxyethoxy), dodecyloxy and octadecyloxy; aryloxy, such as, phenoxy, benzyloxy, naphthoxy; alkoxyalkyl, such as, methoxyethyl, dodecyloxyethyl; halo such as, fluoro, bromo, and chloro; sulfo; carboxy; hydroxy; and amino including mono- and disubstituted amino, e.g., N-alkyl amino and N,N'-dialkylamino.

For use as optical filter agents in photographic processes, such as, diffusion transfer processes employing highly alkaline processing solutions, it may be desirable that the indicator dye selected as the optical filter agent possess a relatively high pKa so that the dye will be in a light-absorbing form during the initial stages of processing and yet may be rendered substantially non-light absorbing within a relatively brief interval as the pH subsequent to substantial image formation is reduced in order to permit early viewing of the image. By substituting a hydrogen bonding group of the above-denoted class on a carbon atom adjacent to the functional proton of a color-producing radical, e.g., the functional —OH group of a p-hydroxycarbocyclic aryl radical or the functional —NH— of the ring of an N-heterocyclic aryl radical, the resulting dyes possess a relatively high pKa which makes them particularly useful as optical filter agents in the aforementioned processes.

The association of two atoms through hydrogen to from a hydrogen bond between or within molecules is well known. When hydrogen is attached to an electronegative atom, for example, O or N, the resultant bond is polarized. If directed toward another atom (M) with an unshared pair of electrons, the hydrogen acts as a bridge between the atoms (O—H . . . M) due to the electrostatic attraction to both atoms between which the hydrogen proton can be transferred. In the present invention an intramolecular hydrogen bond is formed between a hydrogen bonding group of the above-denoted class and an appropriately positioned atom, such as, the —OH and —NH— referred to above to form a 5-, 6- or 7-membered hydrogen-bonded ring.

Depending upon the particular indicator dye, both the A and B radicals may be substituted with hydrogen bonding groups of the above-denoted class, or one of the radicals may be substituted with a hydrogen bonding group of the above-denoted class and the other with a different hydrogen bonding group. Illustrative of such groups are carboxyl; hydroxy; o-hydroxyphenyl; sulfonamido (—NH—SO$_2$—R); and sulfamoyl (—SO$_2$—NH—R$^{oh}$). Suitable R and R$^{oh}$ substituents include branched or straight chain alkyl, preferably alkyl containing 1 to 20 carbon atoms e.g., methyl, ethyl, isopropyl, n-butyl, t-butyl, hexyl, octyl, dodecyl, hexadecyl, octadecyl and eicosanyl; aryl, preferably, phenyl and naphthyl; aralkyl, preferably phenyl-substituted alkyl containing up to 18 carbon atoms, e.g., benzyl, phenethyl, phenylhexyl, phenyloctyl and phenyldodecyl; and alkaryl, preferably alkyl-substituted phenyl containing up to 18 carbon atoms, e.g., p-methylphenyl, p-ethylphenyl, p-hexylphenyl, p-octylphenyl and p-dodecylphenyl.

Specific examples of indicator dyes within the scope of the present invention are as follows:

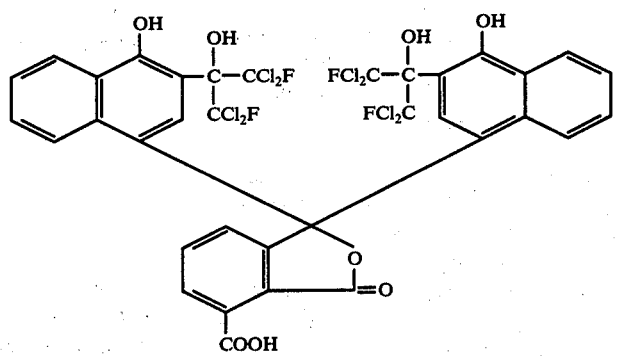

(1)

-continued
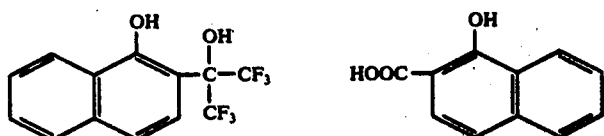
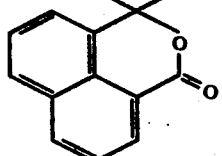
(2)
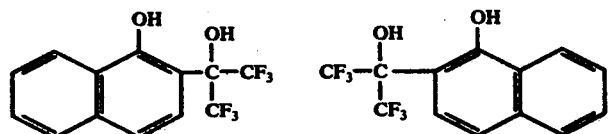
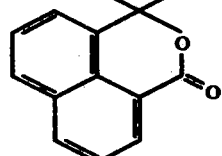
(3)
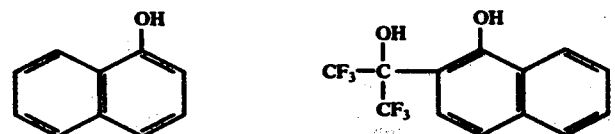
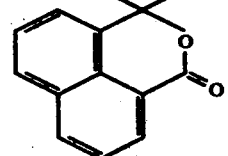
(4)
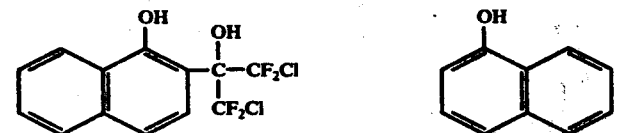
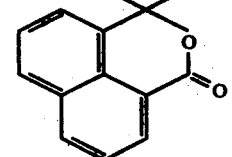
(5)

(6)
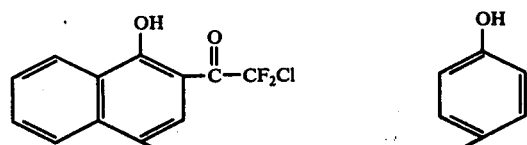
(7)
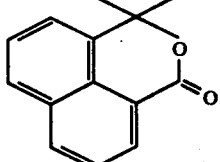
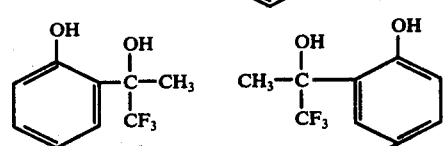
(8)
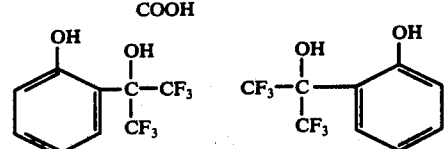
(9)
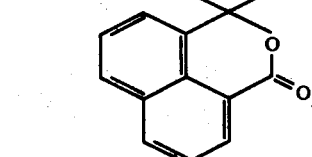
(10)
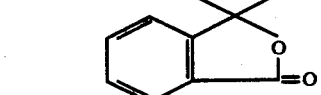
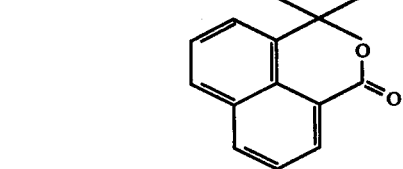

-continued
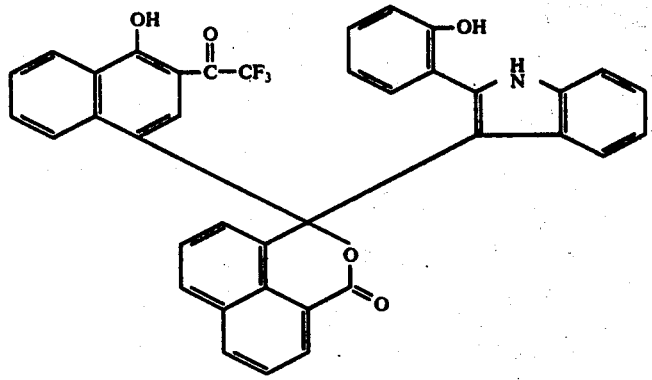
(11)
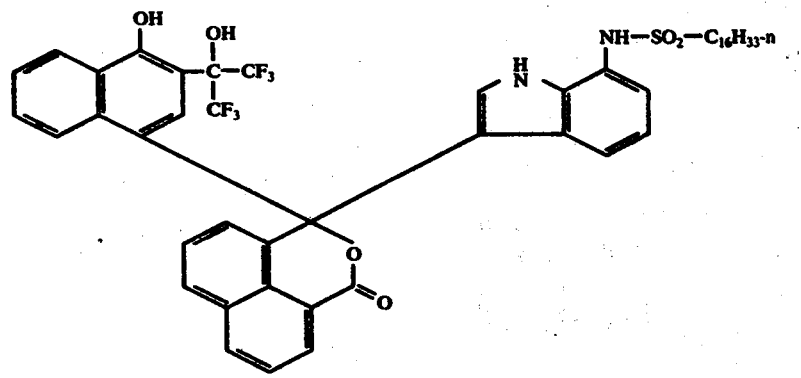
(12)
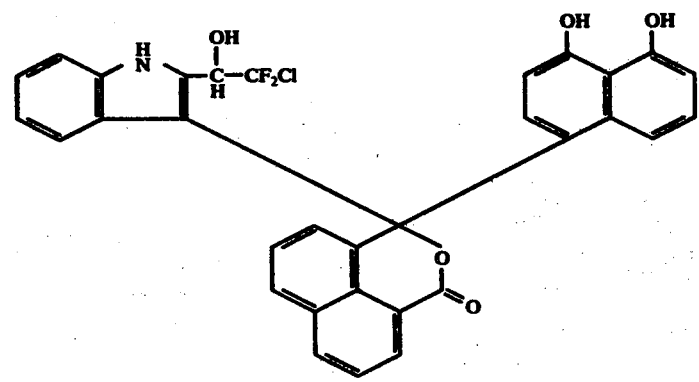
(13)
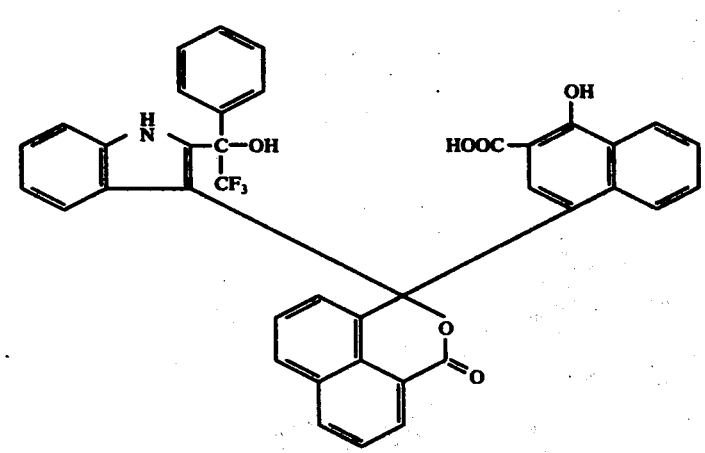
(14)

-continued
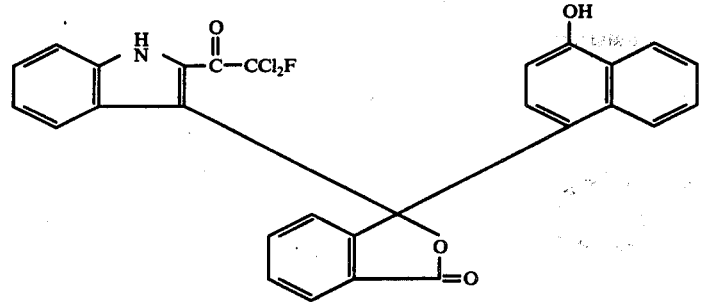 (15)
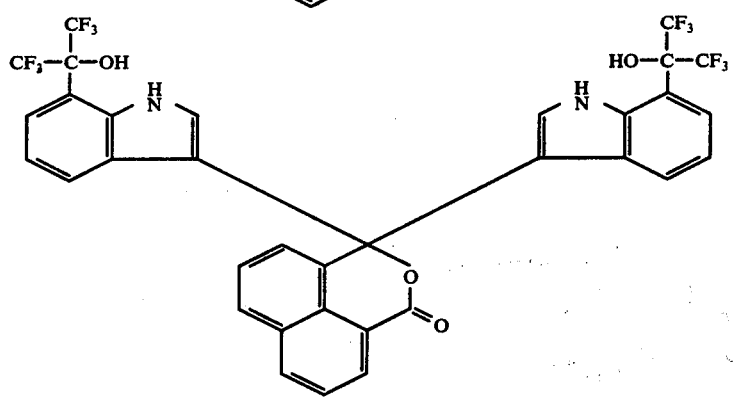 (16)
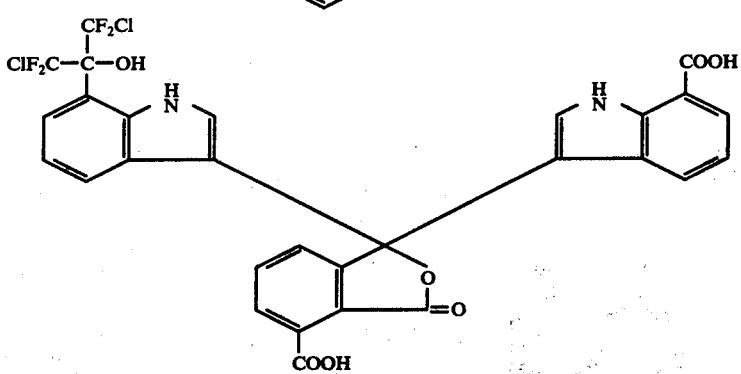 (17)
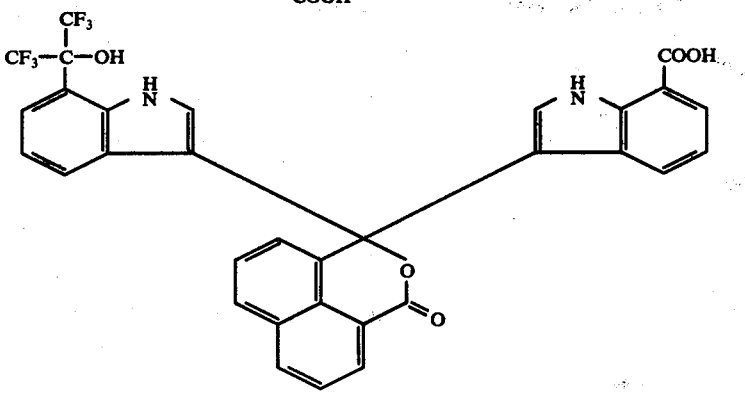 (18)
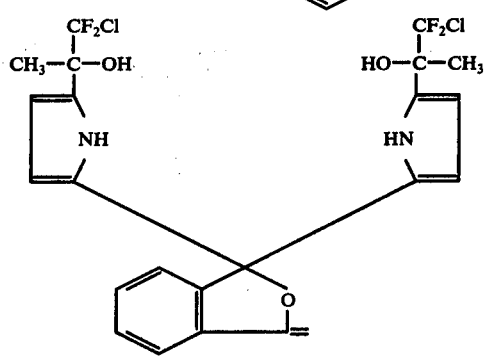 (19)

-continued
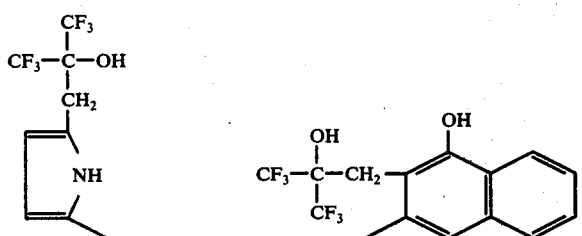 (20)
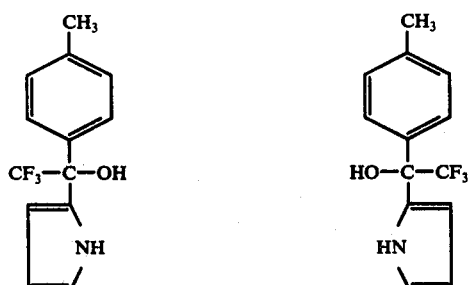 (21)
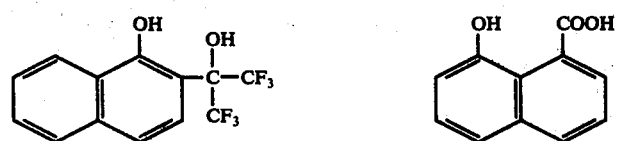 (22)
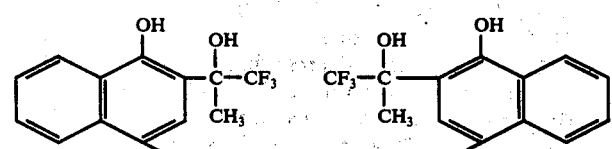 (23)

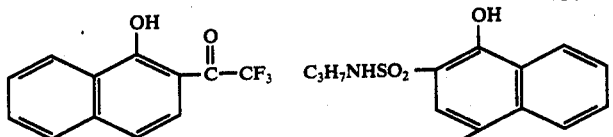 (24)

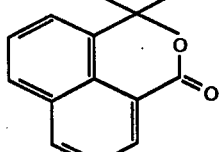

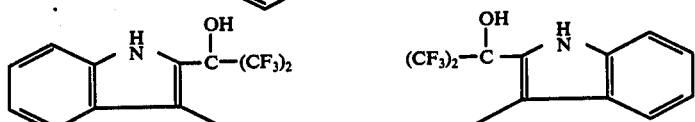 (25)

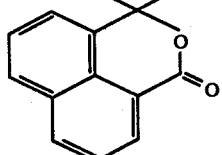

 (26)

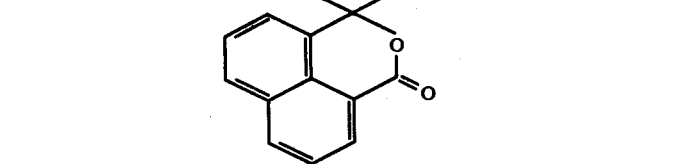 (27)

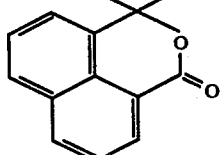

Various methods may be used in the preparation of the indicator dyes described above. One method of preparing these dyes comprises reacting the selected aromatic compound, e.g., an indole or a 1-naphthol with phthalaldehyde or naphthalaldehydic acid in the presence of a mild acid catalyst, e.g., toluene p-sulfonic acid to yield the corresponding 3-(na)phthalidylindole or p-(na)phthalidylnaphthol which is oxidized to a ketol or dehydro intermediate by treating with, for example, dichlorodicyanobenzoquinone. The oxidized intermediate is then reacted with, e.g., a 1-naphthol or an indole in the presence of an acid catalyst to yield the desired dye product. This method of preparing indicator dyes forms the subject matter of copending U.S. patent application Serial No. 108,662 of Alan L. Borror filed Jan. 21, 1971, now abandoned.

Another method of preparing 1-naphthol naphthalides comprises reacting a 3-halo-3-(4'-hydroxynaphthyl)naphthalide and a 1-naphthol in the presence of a heavy metal salt as catalyst. This method forms the subject matter of U.S. Pat. No. 3,772,338 of Richard B. Greenwald.

The following examples are given to further illustrate the present invention and are not intended to limit the scope thereof.

EXAMPLE I

Preparation of the compound of formula (2):

a. Dry 1-hydroxy-2-naphthoic acid (50 gms., 0.266 mole) was suspended in 350 ml. dry benzene in a flame-dried 1 liter 1-neck round bottom flask under an air condenser and drying tube. Thionyl chloride (31.7 gms., 0.266 mole) was added in one portion followed by 1.5 ml. dry N,N-dimethylformamide. The reaction mixture was stirred magnetically 2-3 days at room temperature. Insoluble material (6.5 gms.) was removed by filtration, and the yellow-tan filtrate was evaporated to dryness to give pale yellow 1-hydroxy-2-naphthoyl chloride, m.p. 87°-88° C. Chilled anhydrous methanol (100 ml.) was added quickly to the solid chloride in an exothermic reaction. The partial solution was heated about 5 minutes on the steam bath under a drying tube then allowed to cool. The suspension was chilled and the solid was collected to give 43 gms. (92% by weight) of 1-hydroxy-2-methyl naphthoate.

b. 1-hydroxy-2-methyl naphthoate, (30.2 gms., 0.149 mole) was dissolved in 400 ml. of dry 1,1,2,2-tetrachloroethane in an Erlenmeyer flask fitted with a drying tube. The solution was chilled in an ice bath, and anhydrous aluminum chloride (84 gms., 0.625 mole) was added cautiously in portions. After about one-third of the catalyst was added, vigorous hydrogen chloride evolution ceased so that subsequent addition could be made more rapidly. Nitrobenzene (100 ml.) was added to the chilled dark green suspension, and the mixture was swirled intermittently until a rich brown solution resulted. The complex solution was allowed to stand for about ½ hour before use.

3,3-dichloronaphthalide (37.8 gms., 0.149 mole) was dissolved in 100 ml. of 1,1,2,2-tetrachloroethane in a flame-dried 2 liter 3-neck round bottom flask fitted with an addition funnel, air condenser, mechanical stirrer and drying tube. The solution was chilled in an ice bath; the previously prepared complex solution was decanted into the addition funnel and added dropwise over 30-60 minutes to the well-stirred reaction mixture. A rich purple color developed immediately. The reaction mixture was stirred and allowed to come to room temperature overnight.

Excess ice (300-500 gms.) was added cautiously to the almost solid reaction mixture followed by 20 ml. concentrated hydrochloric acid; the addition funnel and condenser were replaced by a Claisen distillation head, and the organic solvents were distilled with steam. The crude product separated as a yellow-brown solid from the hot dilute acid; it was collected directly, and air dried overnight.

Drying was completed in a vacuum oven, and the dried solid was taken up in hot glacial acetic acid (about 1 g./10 ml.) and insoluble material was removed by filtration; the ketol crystallized on standing and was collected and dried. Trace impurities were removed by solution in hot toluene (about 1 g./5 ml.) from which any insoluble material was separated. Recovery of 3-hydroxy-3-(3'-carbomethoxy-4'-hydroxynapthyl)naphthalide-1,8 was about 50-60% by weight.

c. 3-hydroxy-3-(3'-carbomethoxy-4'-hydroxy-1'-naphthyl)naphthalide-1,8 (50 gms. 0.125 mole) was suspended in dry benzene (500 ml.) in a flame-dried 1 liter round bottom flask fitted with a magnetic stirrer and calcium sulfate drying tube. Thionyl chloride (16.4 gms., 0.137 mole) was added in one portion followed by 2.5 ml. of dry N,N-dimethylformamide. The suspension was stirred at room temperature for 1 day. The 3-chloro-3-(3'- carbomethoxy-4'-hydroxynaphthyl) naphthalide-1,8 product was collected on a Buchner funnel and washed with a small amount of dry hexane. Residual solvent was removed in a vacuum dessicator.

A mixture of 3-chloro-3-(3'-carbomethoxy-4'-hydroxynaphthyl)naphthalide-1,8 (0.84 gms., 2.0 m mole) 2-(bis-trifluoromethyl carbinol)-1-naphthol (0.62 gms., 20 m mole) and silver tetrafluoroborate (0.40 gms., 2.0 m mole) in 75 ml. of dioxane was refluxed for 4 hours. Water (1 ml.) was added to the warm mixture followed by filtration through "Celite". The filtrate was evaporated in vacuo and the residual gum dissolved in approximately 25 ml. of hot benzene. On cooling 1.0 gm. of precipitate was collected and recrystallized from a mixture of 2 ml. of cloroform and 25 ml. of benzene to give 0.8 gm. of solid (melting range 260°-262° C. dec.). The solid obtained (0.5 gm.) was dissolved in 10 ml. of hot ethanol, and the ethanol solution was added to 100 ml. of 15% aqueous potassium hydroxide. The resulting deep blue solution was heated on a steam bath for 2 hours, cooled to room temperature and acidified with 20% hydrochloric acid. After standing for several hours, 0.35 gm. of the title compound was obtained as a white microcrystalline powder (melting point 227° C. dec.).

3-chloro-3-(3'-carbomethoxy-4'-hydroxy-1'-naphthyl) naphthalide also was prepared by oxidizing the 1:1 adduct of 1-hydroxy-2-methyl naphthoate and naphthalaldehydic acid with dichlorodicyanobenzoquinone to give the corresponding 3-hydroxy-3-(3'-carbomethoxy-4'-hydroxy-1'-naphthyl)naphthalide-1,8 which was then treated with thionyl chloride according to the procedure set forth in step c) above to form the corresponding pseudo chloride.

A 3'-carboxy rather than a 3'-carboalkoxy-4'-hydroxy-1'-naphthol naphthalide may be used in the above Example and may be prepared as follows:

The 1:1 adduct of 1-hydroxy-2-naphthoic acid and naphthalaldehydic acid, 0.74 g. (2.0 mmole), was dissolved in 15 ml. of dry tetrahydrofuran and then diluted in 15 ml. of methylene chloride. Dichlorodicyanobenzoquinone, 0.5 g. (2.2 m mole), was added to the solution and the reaction mixture refluxed for 16 hrs. The mixture was filtered and the filtrate taken to dryness. The residue was triturated with methylene chloride and filtered again. Evaporation of solvent left crude quinone methide which was taken up in 10% aqueous sodium hydroxide solution, charcoaled and the ketol acid precipitated by addition of 10% hydrochloric acid to give 0.6 g. of solid. Recrystallization from glacial acetic acid gave 0.45 g. of 3-hydroxy-3-(3'-carboxy-4'-hydroxy-1'-naphthyl) naphthalide-1,8. This ketol was then converted to the corresponding 3-chloro-3-(3'-carboxy-4'-hydroxy-1'-naphthyl) naphthalide-1,8 by treating with thionyl chloride.

The 2-(bis-trifluoromethyl carbinol)-1-naphthol employed in the above Example was prepared as follows:

100 g. (0.7 mole) of 1-naphthol and 6.5 g. of toluene sulfonic acid monohydrate were dissolved in 455 ml. of xylene and heated to 100° C. in a three-neck round-bottom flask fitted with a mechanical stirrer, thermometer, and dry ice condenser. Gaseous hexafluoroacetone was introduced at such a rate that the temperature of the reaction was maintained between 100°-120° to C. After approximately 20 to 30 minutes the reaction temperature began to fall and rapid reflux of excess hexafluoroacetone was noted. The addition was stopped and the mixture heated at 100° C. for 2 hours. The excess gas was allowed to escape with subsequent cooling of the mixture from which the naphthol product crystallized.

This was filtered and about 100 ml. of solvent was evaporated and a second crop collected. Total yield was 107.5 g. (50% by weight) melting range 119°–120° C.

The above method of preparing phenolic derivatives of perhaloacetones is reported by Basil S. Farah et al., J. Org. Chem., vol. 30, p. 1003 (1965). The preparation of aromatic amino derivatives of perhaloacetones is reported by Everett E. Gilbert et al. ibid., p. 1001.

EXAMPLE II

Preparation of the compounds of formula (3):

6.2 g. (0.02 mole) of 2-(bis-trifluoromethyl carbinol)-1-naphthol was suspended in 30 ml. of 1,1,2,2-tetrachloroethane. The suspension was cooled and 16.0 g. (0.12 mole) of anhydrous $AlCl_3$ was added in several portions. To this dark green suspension was added 10 ml. of nitrobenzene. The resulting dark brown suspension was stirred at room temperature for 15 minutes and then added dropwise to a solution of 5.0 g. (0.02 mole) of 3,3-dichloronaphthalide in 20 ml. of 1,1,2,2-tetrachloroethane cooled in an ice bath. The mixture first turned purple and then dark blue. After the addition was complete, stirring was continued for 13 hours at room temperature. Water was carefully added and then the mixture was steam distilled. The remaining solid was filtered, air dried, and then triturated with 200 ml. of hot benzene to give 5.1 g. of cream colored solid, m.p. 207°–210° C. which could be further purified by recrystallization from acetonitrile.

A solution of 0.5 g. of 3-hydroxy-3-(3'-bis-trifluoromethyl carbinol-4'-hydroxy-1'-naphthyl)naphthalide and 0.31 g. of 2-(bis-trifluoromethyl carbinol)-1-naphthol in 15 mls. of phosphorous oxychloride was refluxed for 18 hours. The solution was then taken to dryness in vacuo and the residue treated with a solution of 20% aqueous sodium hydroxide on a steam bath for one-half hour. The deep green solution was cooled and acidified to give the indicator as a gummy solid. TLC indicated purity was approximately 30–40%.

EXAMPLE III

Preparation of the compound of formula (22):

The procedure of Example II was repeated except that 8-carboxy-1-naphthol was substituted for 2-(bis-trifluoromethyl carbinol)-1-naphthol.

As illustrated in the following examples, the indicator dyes of formulae (10) and (12) were prepared by reacting 3-hydroxy-3(3'-bis-trifluoromethyl carbinol-4'-hydroxy-1'-naphthyl)naphthalide and the appropriate indole in the presence of an acid catalyst. The compound of formula (18) was prepared by reacting the oxidation product of 3-naphthalidyl-7-carboxyindole with the bis-trifluoromethyl carbinol substituted indole.

EXAMPLE IV

Preparation of the compound of formula (10):

A solution of 3-carboxyindole (0.16 g., 0.001 mole) and 3-hydroxy-3-(3'-bis-trifluoromethyl carbinol-4'-hydroxy-1'-naphthyl)naphthalide (0.5 g., 0.001 mole) in 5 mls. of phosphorous oxychloride was stirred overnight at room temperature, precipitated onto ice and stirred to hydrolyze the solvent. The crude solid product was collected and found by TLC to be predominantly the title compound.

EXAMPLE V

Preparation of the compound of formula (12):

The procedure of Example IV was repeated except that 7-n-hexadecyl sulfonamidoindole was substituted for 7-carboxyindole to give the title compound.

EXAMPLE VI

Preparation of the compound of formula (18):

7-(bis-trifluoromethyl carbinol)indole (1.6 g., 0.05 mole) and 3-(7-carboxyindol-3-yl)dehydronaphthalide (1.9 g., 0.0055 mole) were dissolved in 20 cc. of a 10% by weight solution of toluenesulfonic acid in acetic acid. The solution was heated at 60° C. for three hours, poured into 100 cc. of water, filtered and recrystallized from toluene to give 1.1 g. of the title compound as a pink solid.

The 7-(bis-trifluoromethyl carbinol)indole was prepared as follows:

Bromoindoline (16 g., 0.081 mole) was dissolved in 70 cc. xylene. 1.5 g. of toluene sulfonic acid was added, and the mixture was heated to 100° C. (internal temperature). Hexafluoroacetone (about 0.081 mole) was condensed on a dry ice condenser, and added dropwise to the above solution. After one-half hour of slow addition, the temperature dropped. The gas flow was then cut off, and the solution was heated for an additional one-half hour. The solution was cooled and evaporated to dryness. The residue was recrystallized from cyclohexane to give 2 g. of a tan solid, m.p. > 200° C.

The tan solid (1.41. g., 0.05 mole) was dissolved in 25 mls. of xylene at 90° C. 2,3-dichloro-5,6-dicyanobenzoquinone (1.14 g., 0.05 mole) was added and the solution was kept at 90° C. for 20 minutes after which it was filtered, extracted with 1N NCl and evaporated. The residue was taken up with 2N NaOH, neutralized with acetic acid and extracted with ether. The ether was evaporated and the residue was triturated with cyclohexane. The oil slowly crystallized to give the 7-(bis-trifluoromethyl carbinol)indole as a white solid, m. p. 160° C. (dec.).

The 3-(7-carboxyindol-3-yl)dehydronaphthalide was prepared by heating a mixture of 7-carboxyindole (0.0372 mole) and naphthaldehydic acid (0.0372 mole) in 38 mls. of glacial acetic acid to reflux with stirring. To this solution, 38 mls. of 12% toluene-p-sulfonic acid in acetic acid was added dropwise. The mixture was cooled to room temperature, filtered, and the 3-naphthalidylindole washed with acetic acid, stirred in acetone, filtered and dried to give a white crystalline solid. The white solid (0.028 mole) and 140 mls. of dioxane were refluxed with stirring under nitrogen. To the solution was added (0.032 mole) of 2,3-dichloro-5,6-dicyano-1,4-benzoquinone and the refluxing was continued for 3.5 hours. The mixture was cooled to room temperature and the product collected by suction filtration.

It will be appreciated that 1-naphthols substituted with the above-denoted hydrogen bonding groups, like the indoles, may be reacted with phthaldehydic or naphthaldehydic to form the corresponding 1:1 adduct which adduct is then oxidized to the corresponding dehydro and/or ketol intermediate. For example, the naphthalidyl adduct of 2-(α-hydroxy-β,β, β-trifluoroethyl)-1-naphthol was prepared by heating a solution of said naphthol (0.02 mole) and naphthaldehydic acid (0.02 mole) in 30 mls. of 12% p-toluenesulfonic acid acetic acid at reflux for about one-half hour, cooling the reaction mixture and collecting the adduct as a white crystalline solid. After recrystallization from acetic acid, the adduct (0.003 mole) and 2,3-dichloro-5,6- dicyanobenzoquinone (0.003 mole) in 15 mls. of dry dioxane were heated together at 70° C. for three hours and then allowed to stand overnight at room temperature. The reaction mixture was chilled to about 10° C., insoluble material was collected and the solvent removed in vacuo to give a tan taffy which was warmed briefly with 5% hydrochloric acid and extracted into ether. The dried ether solution was evaporated to give a yellow solid which was shown by TLC to be a mixture of three compounds, one of which was the ketol, i.e., 3-hydroxy-3-(3'-α-hydroxy-$\beta,\beta,\beta$-trifluoroethyl-4'-hydroxy-1'-naphthyl)naphthalide as characterized by reaction with boron trifluoride.

The above procedure was repeated using as the naphthol, 2-(α-hydroxy-$\beta,\beta,\beta$-chlorodifluorothyl)-1-naphthol to give the corresponding naphthalidyl adduct and then the corresponding ketol oxidation product.

The pH sensitive indicator dyes of the present invention may be used as optical filter agents in any photographic process including conventional tray processing and diffusion transfer photographic techniques. In such processes, the dye or dyes during development of a selectively exposed photosensitive material will be in a position and in a concentration effective to absorb a given level of non-selective radiation incident on and actinic to the photosensitive material. The dyes may be initially disposed in the film unit, for example, in a layer(s) coextensive with one or both surfaces of the photosensitive layer. Where selective exposure of the photosensitive material is made through a layer containing the indicator dye, then the dyes should be in a non-light-absorbing form until the processing solution is applied. Alternately, the dyes may be initially disposed in the processing composition in their light-absorbing form, for example, in the developing bath in tray processing or in the layer of processing solution distributed between the photosensitive element and the superposed image receiving element (or spreader sheet) in diffusion transfer processing. The particular indicator dye or dyes selected should have an absorption spectrum corresponding to the sensitivity of the photosensitive layer, so as to afford protection over the predetermined wavelength range required by the particular photosensitive material employed and should have a pka such that they are in their colored form, i.e., light-absorbing form at the pH at which the photographic process is performed. Most commercially useful photographic processes are performed under alkaline conditions. Diffusion transfer processes, for example, usually employ highly alkaline processing solutions having a pH in excess of 12.

In photographic processes where the optical filter agent is retained in a stratum through which the final image is to be viewed, the color of the indicator dye may be discharged subsequent to image formation by adjusting the pH of the system to a value at which the dye is substantially non-light absorbing in the visible spectrum. In photographic processes performed at an alkaline pH, the optical filter agent, such as, a dye or dyes of the present invention are rendered substantially colorless by reducing the environmental pH. In processes where the optical filter agent is removed or separated from the layer containing the final image or retained in a layer that does not interfere with viewing of the final image, it is unnecessary to convert the indicator dye to its non-light-absorbing form, though the color may be discharged if desired.

The concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. It has been found, by interposing neutral density (carbon containing) filters over a layer of titanium dioxide, that a transmission density of approximately 6.0 from said neutral density filters was effective to prevent fogging of a diffusion transfer multicolor film unit of the type described in said U.S. Pat. No. 3,415,644 having a transparent support layer and an Equivalent ASA Exposure Index of approximately 75, when processed for one minute in 10,000 foot candles of color corrected light, a light intensity approximating the intensity of a noon summer sun. The transmission density required to protect such a film unit under the stated conditions may also be expressed in terms of the "system" transmission density of all the layers intermediate the silver halide layer(s) and the incident light; the "system" transmission density required to protect color film units of the aforementioned type and photographic speed has been found to be on the order of 7.0 to 7.2. Lesser levels of optical transmission density would, of course, provide effective protection for shorter processing times, lesser light intensities and/or films having lower exposure indices. The transmission density and the indicator dye concentration necessary to provide the requisite protection from incident light may be readily determined for any photographic process by following the above described procedure or obvious modifications thereof.

Since most commercial photographic processes employ photosensitive materials sensitive to and exposable by actinic radiation throughout the visible spectrum, e.g., black-and-white panchromatic silver halide emulsions and multilayer silver halide emulsion elements, it is preferred to use, e.g., a mixture of the subject dyes such that the combination of dyes will afford protection from non-selective incident actinic radiation over the wavelength range of 400 to 700 nm. If desired, the subject dyes may be used in conjunction with a second dye(s) which may be non-color-changing but preferably, is also pH sensitive, i.e., has reversibly alterable spectral absorption characteristics in response to changes in the environmental pH so that it may be rendered light-absorbing or non-light-absorbing as desired. The second dye also may be initially present in the film unit or in the processing composition as discussed above either together with or separate from the subject dyes and subsequent to processing may be removed from the film unit or retained within the film structure, provided it is in a form or position such that it does not interfere with viewing of the image produced.

The dyes of the present invention are especially useful as optical filter agents in diffusion transfer processes, for example, those employing composite diffusion transfer photosensitive elements including a film pack or roll wherein superposed photosensitive and image-receiving elements are maintained as a laminate after formation of the final image. Such elements include at least one transparent support to allow viewing of the final image without destroying the structural integrity of the film unit. Preferably, the support carrying photosensitive layer(s) is opaque and the support carrying the image-receiving layer is transparent and selective photoexposure of the photosensitive layer(s) and viewing of the final image both are effected through the latter support. The final image is viewed as a reflection print, i.e., by reflected light, provided by a reflecting agent initially disposed in the processing composition applied and maintained intermediate the image-receiving and next adjacent photosensitive layer or by a preformed layer of reflecting agent initially positioned intermediate the image-receiving and next adjacent photosensitive layer. It will be understood that a preformed reflecting layer, while it should be capable of masking the photosensitive layer(s) subsequent to image formation, should not interfere with selective photoexposure of the photosensitive material prior to processing.

When utilizing reflection-type composite film units, the indicator dye or dyes employed as the optical filter agent(s) may be positioned initially in a layer of the film unit, e.g., in a layer between the image-receiving and next adjacent photosensitive layer through which photo-exposure is effected provided it is incorporated under conditions, i.e., at a pH such that it will not absorb actinic radiation intended to selectively expose the photosensitive material to form a latent image therein. For example, the optical filter agent may be in a layer coated over either the image-receiving layer or the next adjacent photosensitive layer and should remain substantially non-light-absorbing until a processing composition is applied providing a pH at which the indicator dye is capable of being rapidly converted to its light-absorbing form to provide light protection when the film unit is removed from the camera. Rather than being initially disposed in the film unit, the indicator dye may be initially present in the processing composition applied intermediate the image-receiving and next adjacent photosensitive layer subsequent to photoexposure. The dye, when initially disposed in the processing composition, will be in its light-absorbing form.

The dyes selected as optical filter agents should exhibit at the initial pH of the processing, maximum spectral absorption of radiation at the wavelengths to which the film unit's photosensitive silver halide layer or layers are sensitive, and preferably, should be substantially immobile or non-diffusible in the alkaline processing composition in order to achieve optimum efficiency as a radiation filter and to prevent diffusion of filter agent into layers of the film unit where its presence may be undesirable. Recognizing that the filter agent absorption will detract from image-viewing characteristics by contaminating reflecting pigment background, the selected agents should be those exhibiting major spectral absorption at the pH at which processing is effected and minimal absorption at a pH below that which obtains during transfer image formation. Accordingly, the selected optical agent or agents should possess a pKa below that of the processing pH and above that of the environmental pH subsequent to transfer image formation.

As discussed previously, the concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. In the processes where the indicator dye or dyes selected as optical filter agents are used in conjunction with a reflecting agent or agents, the optical filter agents and reflecting agents together should possess the optical transmission density necessary to protect the photosensitive material for the particular photographic process. The optimum concentration of optical filter agent(s) or filter agent(s) together with reflecting agent(s) may be readily determined empirically for each photographic system.

While substantially any reflecting agent may be employed for the layer of reflecting agent, either preformed or applied as a component of the processing composition, it is preferred to select an agent that will not interfere with the color integrity of the dye transfer image, as viewed by the observer, and, most preferably, an agent which is aesthetically pleasing to the viewer and does not provide a background detracting from the information content of the image. Particularly desirable reflecting agents will be those providing a white background, for viewing the transfer image, and specifically those conventionally employed to provide background for reflection photographic prints and, especially, those agents possessing the optical properties desired for reflection of incident radiation.

As examples of reflecting agents, mention may be made of barium sulfate, zinc sulfide, titanium dioxide, barium stearate, silver flake, silicates, alumina, zirconium oxide, zirconium acetyl acetate, sodium zirconium sulfate, kaolin, mica, and the like.

Illustrative of the photographic use of the indicator dyes of the present invention as optical filter agents, a photographic film unit may be prepared by coating, in succession, on a gelatin subbed, 4 mil. opaque polyethylene terephthalate film base, the following layers:

1. a layer of the cyan dye developer 1,4-bis-($\beta$-[hydroquinonyl-$\alpha$-methyl]-ethylamino)-5,8-dihydroxy-anthraquinone dispersed in gelatin and coated at a coverage of about 80 mgs./ft.$^2$ of dye and about 100 mgs./ft.$^2$ of gelatin;

2. a red-sensitive gelatino-silver iodobromide emulsion coated at a coverage of about 225 mgs./ft.$^2$ of silver and about 50 mgs./ft.$^2$ of gelatin;

3. a layer of the acrylic latex sold by Rohm and Haas Co., Philadelphia, Pa., U.S.A., under the trade designation AC-61 and polyacrylamide coated at a coverage of about 150 mgs./ft.$^2$ of AC-61 and about 5 mgs./ft.$^2$ of polyacrylamide;

4. a layer of the magenta dye developer 2-(p-[$\beta$-hydroquinonylethyl]-phenylazo)-4-isopropoxy-1-naphthol dispersed in gelatin and coated at a coverage of 70 mgs./ft.$^2$ of dye and about 120 mgs./ft.$^2$ of gelatin;

5. a green-sensitive gelatino-silver iodobromide emulsion coated at a coverage of about 120 mgs./ft.$^2$ of silver and 60 mgs./ft.$^2$ of gelatin;

6. a layer comprising the acrylic latex sold by Rohm and Haas Co. under the trade designation B-15 and polyacrylamide coated at a coverage of about 100 mgs./ft.$^2$ of B-15 and about 10 mgs./ft.$^2$ of polyacrylamide;

7. a layer of the yellow dye developer 4-(p-[$\beta$-hydroquinonylethyl]-phenylazo)-3-(N-n-hexyl-carboxamido)-1-phenyl-5-pyrazolone and the auxiliary developer 4'-methylphenyl hydroquinone dispersed in gelatin and coated at a coverage of about 50 mgs./ft.$^2$ of dye, about 15 mgs./ft.$^2$ of auxiliary developer and 50 mgs./ft.$^2$ of gelatin;

8. a blue-sensitive gelatino-silver iodobromide emulsion coated at a coverage of about 75 mgs./ft.$^2$ of silver and about 75 mgs./ft.$^2$ of gelatin; and 9. a layer of gelatin coated at a coverage of about 50 mgs./ft.$^2$ of gelatin.

Then a transparent 4 mil. polyethylene terephthalate film base may be coated, in succession, with the following illustrative layers:

1. a 7:3 mixture, by weight, of polyethylene/ maleic acid copolymer and polyvinyl alcohol at a coverage of about 1400 mgs./ft.$^2$, to provide a polymeric acid layer;

2. a graft copolymer of acrylamide and diacetone acrylamide on a polyvinyl alcohol backbone in a molar ratio of 1:3.2:1 at a coverage of about 800 mgs./ft.$^2$, to provide a polymeric spacer layer; and 3. a 2:1 mixture, by weight, of polyvinyl alcohol and poly-4-vinylpyridine, at a coverage of about 900 mgs./ft.$^2$ and including about 20 mgs./ft.$^2$ phenyl mercapto tetrazole, to provide a polymeric image-receiving layer.

The two components thus prepared may then be taped together in laminate form, at their respective edges, by means of a pressure-sensitive binding tape extending around, in contact with, and over the edges of the resultant laminate.

A rupturable container comprising an outer layer of lead foil and an inner liner or layer of polyvinyl chloride retaining an aqueous alkaline processing solution comprising:

| | | |
|---|---|---|
| Water | 100 | cc. |
| Potassium hydroxide | 11.2 | gms. |
| Hydroxyethyl cellulose (high viscosity) [commercially available from Hercules Powder Co., Wilmington, Delaware, under the trade name Natrasol 250] | 3.4 | gms. |
| N-phenethyl-α-picolinium bromide | 2.7 | gms. |
| Benzotriazole | 1.15 | gms. |
| Titanium dioxide | 50.0 | gms. |
| | 2.0 | grams |

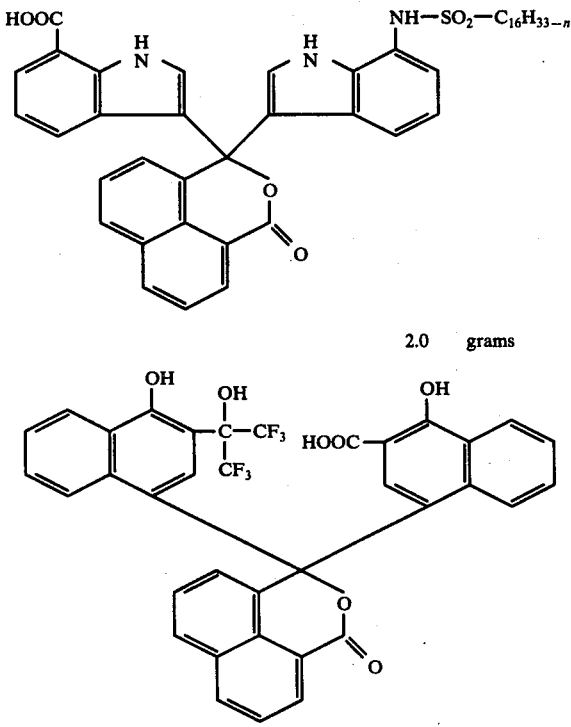

2.0 grams may then be fixedly mounted on the leading edge of each of the laminates, by pressure-sensitive tapes interconnecting the respective containers and laminates, such that, upon application of compressive pressure to a container, its contents may be distributed, upon rupture of the contaner's marginal seal, between the polymeric image-receiving layer and next adjacent gelatin layer.

The photosensitive composite film units may be exposed through step wedges to selectively filter radiation incident on the transparent polyethylene terephthalate layer and processed by passage of the exposed film units through appropriate pressure-applying members, such as suitably gapped, opposed rolls, to effect rupture of the container and distribution of its contents. During processing, the multicolor dye transfer image formation may be viewed through the transparent polyethylene terephthalate layer against the titanium dioxide background provided by distribution of the pigment containing processing composition between the polymeric image-receiving layer and gelatin layer 9 of the photosensitive component. The film unit may be exposed to incident light and the formation of the image may be viewed upon distribution of the processing composition by reason of the protection against incident radiation afforded the photosensitive silver halide emulsion layers by the optical filter agents and by reason of the effective reflective background afforded by the titanium dioxide.

The film unit detailed above is similar to that shown in FIG. 2 and related FIGS. 3 and 4 of aforementioned copending U.S. Patent application Ser. No. 101,968. The negative component of the film unit including the photosensitive strata and associated dye-image-forming material; the positive component including the timing, neutralizing and dyeable layers; and the processing composition including its components, such as, the alkaline material and various addenda are described in detail in application Ser. No. 101,968. For convenience, the specification of this application is specifically incorporated herein.

Besides the above photosensitive element, the dyes of the present invention may be employed in composite photosensitive elements, in general, where the dyeable stratum along with any associated layers may be contaned together with the photosensitive strata as a unitary film unit which may be termed an integral negative-positive film unit comprising a negative component including the aforementioned essential layers and a positive component including at least the dyeable stratum in which the color transfer image is to be formed. The essential layers are preferably contained on a transparent dimensionally stable layer or support member positioned closest to the dyeable stratum so that the resulting transfer image is viewable through this transparent layer. Most preferably another dimensionally stable layer which may be transparent or opaque is positioned on the opposed surface of the essential layers so that the aforementioned essential layers are sandwiched or confined between a pair of dimensionally stable layers or support members, at least one of which is transparent to permit viewing therethrough of a color transfer image obtained as a function of development of the exposed film unit in accordance with the known color diffusion transfer processes. It will be appreciated that all of these film units, like the specific one detailed above, may optionally contain other layers performing specific desired functions, e.g., spacer layers, pH-reducing layers, etc.

Examples of such integral negative-positive film units for preparing color transfer images viewable without separation are those described and claimed in aforementioned U.S. Pat. No. 3,415,644 and in U.S. Pat. Nos. 3,415,645, 3,415,646, 3,473,925, and 3,573,043.

In general, the film units of the foregoing description, e.g., those described in the aforementioned patents and/or copending applications, are exposed to form a developable image and thereafter developed by applying the appropriate processing composition to develop exposed silver halide and to form, as a function of development, an imagewise distribution of diffusible dye image-providing material which is transferred, at least in part by diffusion, to the dyeable stratum to impart thereto the desired color transfer image, e.g., a positive color transfer image. Common to all of these systems is the provision of a reflecting layer between the dyeable stratum and the photosensitive strata to mask effectively the latter and to provide a background for viewing the color image contained in the dyeable stratum, whereby this image is viewable without separation, from the other layers or elements of the film unit. As discussed previously, in some embodiments this reflecting layer is provided prior to photoexposure, e.g., as a preformed layer included in the essential layers of the laminar structure comprising the film unit, and in others it is provided at some time thereafter, e.g., by including a suitable light-reflecting agent, for example, a white pigment, such as, titanium dioxide, in the processing composition. As an example of such a preformed layer, mention may be made of that disclosed in the copending applications of Edwin H. Land, Ser. No. 846,441, filed July 31, 1969, now U.S. Pat. No. 3,615,421 issued Oct. 26, 1971, and Ser. No. 3,645, filed Jan. 19, 1970, now U.S. Pat. No. 3,620,724 issued Nov. 16, 1971. The reflecting pigment may be generated in situ as is disclosed in the copending applications of Edwin H. Land, Ser. Nos. 43,741 and 43,742, both filed June 5, 1970, and both issued on Mar. 7, 1972 as U.S. Pat. Nos. 3,647,434 and 3,647,435, respectively. In a particularly preferred form, such film units are employed in conjunction with a rupturable container, such as, that used above, containing the processing composition having the light-reflecting agent incorporated therein which container is adapted upon application of pressure of distributing its contents to develop the exposed film unit and to provide the light-reflecting layer.

As noted previously, the photographic use of the dyes of the present invention as optical filter agents to prevent post-exposure fogging of a selectively exposed photosensitive material is not limited to diffusion transfer processes nor to such processes employing composite photosensitive elements. While the use of such dyes in composite multicolor diffusion transfer film units is a particularly preferred embodiment of the present invention, these dyes may be used with equally effective results in any photographic process where it is desired to protect a photosensitive material from incident radiation actinic to the photosensitive material within the wavelength range capable of being absorbed by the dye. For example, the subject dyes may be used in conventional tray photographic processing as a component of the processing bath, or they may be present in a layer coextensive with one or both surfaces of a layer of photosensitive material to be processed using conventional tray procedures, provided that they are non-light-absorbing prior to photoexposure and also subsequent to developing the latent image unless the layer containing the dye is to be removed subsequent to processing. In such procedures, the photo-exposed photosensitive material will, of course, be transferred from the camera to the processing bath in the absence of radiation actinic to the material.

The subject dyes also may be employed in diffusion transfer processes where the photosensitive and image-receiving elements are separated subsequent to the formation of a transfer image or where a spreader sheet is separated from the photosensitive element to reveal a final image in the negative. In addition to the composite diffusion transfer structures described above, the subject dyes may be used with composite diffusion transfer film units where the final image is to be viewed by transmitted light. Also they may be used in composite film units specifically adapted, for example, for forming a silver transfer image, for developing a negative silver image by monobath processing, for obtaining an additive color image, and for obtaining a dye image by the silver dye bleach process which structures are described in detail in aforementioned copending U.S. application Ser. No. 101,968, particularly with reference to FIGS. 10 to 13 of the application's drawings.

Although the invention has been discussed in detail throughout employing dye developers, the preferred image providing materials, it will be readily recognized that other, less preferred, image-providing materials may be substituted in replacement of the preferred dye developers in the practice of the invention. For example, there may be employed dye image-forming materials such as those disclosed in U.S. Pat. Nos. 2,647,049; 2,661,293; 2,698,244; 2,698,798; 2,802,735; 3,148,062; 3,227,550; 3,227,551; 3,227,552; 3,227,554; 3,243,294; 3,330,655; 3,347,671, 3,352,672; 3,364,022; 3,443,939; 3,443,940; 3,443,941; 3,443,943; etc., wherein color diffusion transfer processes are described which employ color coupling techniques comprising, at least in part, reacting one or more color developing agents and one or more color formers or couplers to provide a dye transfer image to a superposed image-receiving layer and those disclosed in U.S. Pat. No. 2,774,668 and 3,087,817, wherein color diffusion transfer processes are described which employ the imagewise differential transfer of complete dyes by the mechanisms therein described to provide a transfer dye image to a contiguous image-receiving layer, and thus including the employment of image-providing materials in whole or in part initially insoluble or nondiffusible as disposed in the film unit which diffuse during processing as a direct or indirect function of exposure.

In view of the foregoing, it will be readily apparent that the subject dyes are useful generally in photographic processes for producing silver, monochromatic and multi-color images using any photosensitive material including conventional and direct positive silver halide emulsions. Depending upon the selected photosensitive material, one or more of the dyes may be used alone or in combination with another optical filter agent, such as another light-absorbing dye, which second dye may be non-color-changing or another pH sensitive dye. If the selected dye or dyes do not possess the desired stability in the processing composition for long term storage therein, they may be initially disposed in the film structure or stored in a double-compartmented pod or in one of two associated pods separate from the processing solution until such time as the pod(s) are ruptured whereupon the dyes are admixed with the processing solution.

Since certain changes may be made in the above product and process without departing from the scope of the invention herein involved, it is intended that all matter contained in the above description or shown in the accompanying drawings shall be interpreted as illustrative and not in a limiting sense.

What is claimed is:

1. An indicator dye having the formula

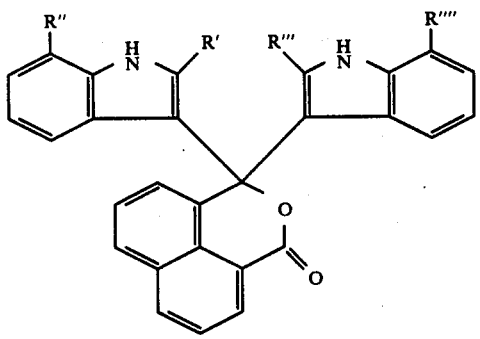

wherein R' and R" each are selected from hydrogen, carboxy, hydroxy, o-hydroxyphenyl, —NH—SO₂—R wherein R is alkyl containing 1 to 20 carbon atoms, aryl selected from phenyl and naphthyl, alkyl-substituted phenyl containing up to 18 carbon atoms or phenyl-substituted alkyl containing up to 18 carbon atoms, —SO₂—NH—R° wherein R° has the same meaning as R, and the group

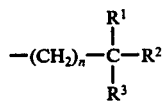

wherein $R^1$ is —OH, $R^2$ is hydrogen, alkyl having 1 to 20 carbon atoms, aryl selected from phenyl and naphthyl, alkyl-substituted phenyl having up to 20 carbon atoms or perhalomethyl, $R^1$ and $R^2$ when taken together represent =O, $R^3$ is perhalomethyl, and $n$ is an integer 0 or 1, at least one of R' and R" being hydrogen and one of R''' and R'''' being said group

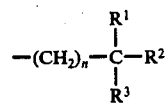

and the other being hydrogen.

2. An indicator dye as defined in claim 1 wherein said R''' is hydrogen.

3. An indicator dye as defined in claim 2 wherein said $R^2$ of said R'''' group is perhalomethyl.

4. An indicator dye as defined in claim 3 wherein said R'''' group is

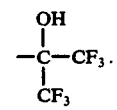

5. An indicator dye as defined in claim 4 wherein R' is hydrogen.

6. The compound of the formula

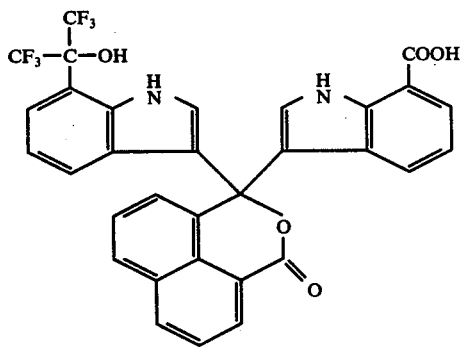

* * * * *